(12) United States Patent
Wilson et al.

(10) Patent No.: US 7,319,002 B2
(45) Date of Patent: Jan. 15, 2008

(54) METHOD FOR PURIFICATION OF VIRAL VECTORS HAVING PROTEINS WHICH BIND SIALIC ACID

(75) Inventors: James M. Wilson, Gladwyne, PA (US); Alberto Auricchio, Naples (IT); Markus Hildinger, Boston, MA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 542 days.

(21) Appl. No.: 10/485,893

(22) PCT Filed: Aug. 6, 2002

(86) PCT No.: PCT/US02/25096

§ 371 (c)(1), (2), (4) Date: Feb. 4, 2004

(87) PCT Pub. No.: WO03/014367

PCT Pub. Date: Feb. 20, 2003

(65) Prior Publication Data

US 2004/0191762 A1    Sep. 30, 2004

Related U.S. Application Data

(60) Provisional application No. 60/310,772, filed on Aug. 8, 2001.

(51) Int. Cl.
  *C12N 15/864*   (2006.01)
  *C12N 7/02*     (2006.01)
  *C12N 1/02*     (2006.01)
  *C07K 1/14*     (2006.01)
  *C07K 1/22*     (2006.01)
  *C07K 17/02*    (2006.01)
  *A61K 48/00*    (2006.01)

(52) U.S. Cl. .............................. 435/5; 435/6; 435/239; 435/235.1; 435/308.1; 530/344; 530/350; 530/395; 530/413

(58) Field of Classification Search ...................... None
See application file for complete search history.

(56) References Cited

U.S. PATENT DOCUMENTS

| 4,355,102 A | * | 10/1982 | Quash ............................. 435/5 |
| 5,580,776 A |   | 12/1996 | Wilson et al. |
| 6,001,557 A |   | 12/1999 | Wilson et al. |
| 6,383,795 B1 |   | 5/2002 | Carrion et al. |
| 6,399,385 B1 |   | 6/2002 | Croyle et al. |
| 6,485,958 B2 |   | 11/2002 | Blanche et al. |
| 2003/0228282 A1 |   | 12/2003 | Gao et al. |

FOREIGN PATENT DOCUMENTS

| WO | WO 98/22588 A2 | 5/1998 |
| WO | WO 02/44348 A2 | 6/2002 |
| WO | WO 03/052051 A2 | 6/2003 |

OTHER PUBLICATIONS

Maruyama et al., PNAS, 1994, vol. 91, pp. 8273-8277.*
Auricchio, A., et al, *A Single-Step Affinity Column for Purification of Serotype-5 Based Adeno-associated Viral Vectors*, Molecular Therapy, Oct. 2001, pp. 372-374, vol. 4, No. 4, XP002297593.
Walters, Robert W., et al, *Secreted and Transmembrane Mucins Inhibit Gene Transfer with AAV4 More Efficiently than AAV5*, The Journal of Biological Chemistry, Jun. 28, 2002, pp. 23709-23713, vol. 277, No. 26, XP002297592.
Walters, Robert W., et al, *Structure of Adeno-Associated Virus Serotype 5*, Journal of Virology, Apr. 2004, pp. 3361-3371, vol. 78, No. 7, XP009037084.
Kaludov, N., et al, *Production, purification and preliminary X-ray crystallographic studies of adeno-associated virus serotype 4*, Virology, Feb. 1, 2003, pp. 1-6, vol. 306, XP002297596.
Auricchio, A., et al, *Isolation of Highly Infectious and Pure Adeno-Associated Virus Type 2 Vectors with a Single-Step Gravity-Flow Column*, Human Gene Therapy, Jan. 1, 2001, pp. 71-76, vol. 12, XP002297594.
Kaludov et al, Adeno-Associated Virus Serotype 4 (AAV4) and AAV5 Both Require Sialic Acid binding for Hemagglutination and Efficient Transduction but Differ in Sialic Acid Linkage Specificity, Journal of Virology, vol. 75, No. 15, pp. 6884-6893, (Aug. 2001).
Walters et al, Binding of Adeno-Associated Virus Type 5 to 2,3-Linked Sialic Acid is Required for Gene Transfer, The Journal of Biological Chemistry, vol. 276, No. 23, pp. 20610-20616, (Jun. 8, 2001).

* cited by examiner

*Primary Examiner*—David Guzo
(74) *Attorney, Agent, or Firm*—Howson & Howson LLP

(57) ABSTRACT

A method for isolating, from a mixture, a virus having a surface protein with a binding site for sialic acid is provided. The method involves contacting the mixture with mucin which has been linked to a solid support and washing the solid support to remove material from the mixture is non-specifically bound to the mucin-linked support. Thereafter, the specifically bound virus (e.g., AAV4 or AAV5) may be removed in a further washing step utilizing a concentrated slat or solution with low pH. Also described are pharmaceutical kits containing solid supports linked to mucin for use in isolating virus having a surface protein with a binding site for sialic acid, or detecting the presence of the virus in a biological sample.

19 Claims, No Drawings

METHOD FOR PURIFICATION OF VIRAL VECTORS HAVING PROTEINS WHICH BIND SIALIC ACID

STATEMENT REGARDING FEDERALLY SPONSORED RESEARCH OR DEVELOPMENT

This work was supported, in part, by funding by the National Institutes of Health, P30 DK47757. The US Government may have certain rights in this invention.

CROSS-REFERENCE TO RELATED APPLICATIONS

This is a US National Phase of Application No. PCT/US02/25096, filed Aug. 6, 2002, which claims the benefit under 35 USC 119(e) of US Provisional Appln. No. 60/310,772, filed on Aug. 8, 2001.

BACKGROUND OF THE INVENTION

Gene therapy vectors based on adeno-associated virus (AAV) serotype 2 have emerged as being preferred for achieving stable transduction following in vivo administration. However, while stability of transgene expression was impressive, its efficiency often was not.

Basic research and commercial development of vectors based on serotype 2 has been enhanced with the development of chromatographic methods for purification. With the development of other AAV serotype vectors has flowed the need for methods of purification of such vectors. One such vector, AAV serotype 5 (AAV5) has emerged as a useful vector. To date, however, purification of AAV5 based vectors required cesium chloride ($CsCl_2$) sedimentation, since it does not bind heparin which has been used for purification of AAV2. $CsCl_2$ sedimentation is time consuming, not scalable, and yields preparations that are heavily contaminated with cellular proteins.

What are needed are methods of purification for AAV5-based vectors which are rapid and may be readily scaled-up for use in production.

SUMMARY OF THE INVENTION

The present invention provides a rapid method for identifying and purifying AAV4 and AAV5 viral vectors from cultures and other solutions containing cellular and other viral materials.

Thus, in one aspect, the invention provides a method for isolating a construct which has a capsid (or envelope) protein with a binding site for sialic acid. The method of the invention is particularly well suited from isolating constructs containing adeno-associated virus (AAV) serotype 4 (AAV4) or AAV serotype 5 (AAV5) capsid proteins. The method involves contacting the solution containing the AAV4 or AAV5 with sialic acid which has been linked to a solid support. Thus, the construct having a capsid protein having a binding site for sialic acid is selectively bound by the sialic acid-linked molecule.

In a preferred embodiment, the method of the invention involves allowing a mixture which contains the AAV to contact mucin which has been linked to a solid support. Thereby, the AAV is selectively bound by the mucin-linked support. Thereafter, the solid support is washed to remove material from the mixture which is non-specifically bound to the mucin-linked support.

In another aspect, the invention provides a kit useful for separating AAV4 or AAV5 comprising a liquid chromatography column or a solution containing a solid support having mucin linked thereto.

In still another aspect, the invention provides a kit useful for detecting the presence of AAV4 or AAV5 in a biological sample. Such a kit contains a solid support having a molecule comprising sialic acid linked thereto and a reagent which permits visual detection of binding of said AAV4 or AAV5 to the molecule.

Still other aspects and advantages of the present invention will be readily apparent from the following detailed description of the invention.

DETAILED DESCRIPTION OF THE INVENTION

The present invention provides a method for isolation and detection of viruses having surface proteins which specifically bind sialic acid (such as AAV4 or AAV5) by using mucin attached to a solid support. Removal of the specifically bound viruses by elution or incubation with a high salt solution efficiently recovers highly active viruses of greater purity than is achieved with $CsCl_2$ sedimentation. The isolated viruses are highly infectious and purer than those isolated using conventional $CsCl_2$ gradients. In addition, this technique is fast, does not require special equipment and can be easily scaled-up. These are important characteristics for production of high-quality viruses to be used from bench to bedside. The invention further provides kits useful for isolation and detection of viruses using the methods described herein, which utilize a single step affinity column for purification and detection of viral vectors and, optionally, a visually detectable marker system.

These and other aspects of the invention are described in detail herein.

Purification Targets

The method of the invention is particularly well suited for separation and isolation of viral vectors having capsids composed of AAV serotype 5 capsid proteins or AAV serotype 4 capsid proteins. The inventors have found that these AAV serotypes can be readily separated from the materials found in the cultures in which these viruses are produced by the ability of their capsids to specifically bind 2,3-sialic acid. In contrast, the other materials (e.g., cellular and other viral proteins) found in helper-free production cultures for AAV do not specifically bind sialic acid. Similarly, the method of the invention is useful for separation and isolation of AAV4 or AAV5 capsid proteins from helper-dependent production cultures, as adenoviruses, AAV1, and the other cellular materials found in such cultures do not specifically bind sialic acid.

In addition, the method of the invention may also be readily applied to purification of any viruses encapsidated or enveloped in a protein which contains binding sites for sialic acid, or to other types of proteins which contain binding sites for sialic acid. For example, it will be readily understood that viral vectors containing chimeric capsid or envelope proteins, e.g., those containing portions of AAV5 and/or AAV4 capsid protein which have sialic acid binding sites, or viral vectors pseudotyped in an AAV4, AAV5 or chimeric capsid, can be detected, separated and isolated according to the invention. Still other viral vectors, chimeric proteins, or protein fragments may be separated, isolated, and/or purified according to the invention. Given the information provided herein, it is well within the ability of one of skill in the art to determine whether a selected capsid protein or other protein specifically binds to sialic acid. For convenience throughout this specification, these viral vectors (e.g., AAV4 and AAV4) and other proteins which have binding sites specific for sialic acid as described herein, are termed "purification targets".

Sialic Acid-containing Molecules.

For use in the present invention, one or more sialic acid molecules may be bound directly or indirectly (e.g., via a suitable linker) to a solid support, as defined herein. Alternatively, sialic acid can be found in a variety of proteinaceous and chemical molecules which can be bound (directly or indirectly) to a solid support. Such molecules may be obtained from a variety of natural, synthetic, recombinant or other suitable methods.

An example of a proteinaceous molecule containing sialic acid is mucin. Mucin is a mammalian protein present in saliva, intestinal juice and other secretions that is highly enriched in sialic acid. A variety of mucin proteins are known and may be readily used in the methods and compositions of the invention. Alternatively, fragments of mucins or other molecules which contain sialic acid may be readily utilized. See, e.g., Gendler S J, et al. Molecular cloning and expression of human tumor-associated polymorphic epithelial mucin. *J. Biol. Chem.* 265: 15286 (1990); Siddiqui J, et al., Isolation and sequencing of a cDNA coding for the human DF3 breast carcinoma-associated antigen. *Proc. Natl. Acad Sci. USA* 85: 2320 (1988); Ligtenberg M J L, et al., Episialin, a carcinoma-associated mucin, is generated by a polymorphic gene encoding splice variants with alternative amino termini. *J. Biol. Chem.* 265: 5573 (1990) pancreas; Gum J R, et al, Molecular cloning of cDNAS derived from a novel human intestinal mucin gene. *Biochem. Biophys. Res. Commun.* 171: 407 (1990); small intestine, Gum J R, et al., Molecular cloning of human intestinal mucin cDNAs. Sequence analysis and evidence for genetic polymorphism. *J. Biol. Chem.* 264: 6480 (1989); Gum J R, et al., Molecular cloning of cDNAS derived from a novel human intestinal mucin gene. *Biochem. Biophys. Res. Commun.* 171: 407 (1990); and bronchoepithelial cell mucin, Porchet N, et al, Molecular cloning and chromosomal localization of a novel human tracheo-bronchial mucin CDNA containing tandemly repeated sequences of 48 base pairs. *Biochem. Biophys. Res. Commun.* 175: 414 (1991). Sequences for mucins may be obtained from a variety of computer databases, including GenBank and PubMed. These and other mucins may be purified from natural sources, produced recombinantly, or generated synthetically.

Chemical synthesis of mucin, a sialic acid-rich fragment thereof, or other peptides are well known in the art, such as TBOC or FMOC protection of alpha-amino groups. (See, Coligan, et al., *Current Protocols in Immunology*, Wiley Interscience, 1991, Unit 9). Alternatively, peptides can also be synthesized by the well known solid phase peptide synthesis methods (Merrifield, *J. Am. Chem. Soc.*, 85:2149 (1962); Stewart and Young, Solid Phase Peptide Synthesis (Freeman, San Francisco, 1969) pp. 27-62).

Alternatively, a chemical molecule may be utilized which contains one or more sialic acid moieties, such that the chemical molecule is attached to a solid support. In yet another alternative, a solid support for use in purification may be chemically or otherwise modified to contain one, and preferably more than one, sialic acid moieties. Such sialic acid moieties may be directly linked to the solid support, e.g., by a covalent bond or other suitable bound which withstands binding of the sialic acid to the purification target and removal of non-specifically bound materials. Alternatively, the sialic acid moieties may be indirectly linked to the solid support, e.g., by a moiety which facilitates binding of the sialic acid to the support. Such a moiety may be a protein, a chemical moiety, or another suitable linker.

Desirably, the solid support and/or the molecule containing sialic acid contains 2,3-O-sialic acid and 2,3-N-sialic acid, or more than one of either or both moieties. A solid support (and/or molecule containing sialic acid) contains one or more 2,3-O-sialic acid moieties, is particularly well suited for use when the purification target is derived from AAV4. In still another embodiment, a solid support (and/or molecule containing sialic acid) which contains one or more 2,3-N-sialic acid moieties is particularly well suited for use when the purification target is derived from AAV4.

Methods for attaching the sialic acid moieties and/or the molecules containing sialic acid, directly or indirectly, to the solid support are known to those of skill in the art.

Solid Supports

The mucin, or other molecule carrying sialic acid, is desirably linked to a solid support which can be used for binding of the purification target (e.g., AAV4). For convenience, reference will be made to mucin. However, one of skill in the art will understand that any other of the molecules carrying sialic acid may be substituted in the invention. In one particularly desirable embodiment, the mucin is covalently bound to the solid support. Suitable methods are known in the art, and are also available from the manufacturers of solid supports.

As used herein, the term "solid support" refers to any substance, including gels, resins, beads, powders and other solids, to which sialic acid or a molecule containing sialic acid(s) can be bound so that the sialic acid molecule bond to the solid support withstands binding of the sialic acid to the purification target and removal of non-specifically bound materials. Examples of suitable solid supports include resins composed of sepharose, agarose, activated agarose cross-linked agarose, mixed agarose-polyacrylamide, or polyacrylein; beads (including microbeads); silicon; glass; microcells; microcapsules; microtiter plates; and biochips. Useful supports include those described in International Patent Publication WO 99/27351, published Jun. 3, 1999; International Patent Publication WO 99/27140, published Jun. 3, 1999; U.S. Pat. No. 6,096,273; International Patent Publication WO 00/14197, published Mar. 16, 2000, among others.

A variety of microbeads are known, including the aminodextran beads described in U.S. Pat. Nos. 6,074,884; 5,945,293; and 5,658,741. Aminodextran-coated monodispersed colloidal dispersions of magnetic ferrite [U.S. Pat. No. 5,240,640]; metal [U.S. Pat. No. 5,248,772]; polystyrene [U.S. Pat. No. 5,466,609; U.S. Pat. No. 5,707,877; U.S. Pat. No. 5,639,620; U.S. Pat. No. 5,776,706], and polystyrene-metal [U.S. Pat. No. 5,552,086; U.S. Pat. No. 5,527,713] particles may also be employed as solid supports according to this invention. Another type of solid support may contain the above-described coated substrate with a layer of colloidal-sized metallic solid overlaying the aminodextran coating. Gold/silver colloid coated polystyrene-aminodextran beads, their preparation, characterization and use in analyses of subpopulations of white blood cells in whole blood have been described. See, e.g., U.S. Pat. No. 5,248,772; U.S. Pat. No. 5,552,086; U.S. Pat. No. 5,945,293; O. Siiman and A. Burshteyn, *J. Phys. Chem.*, 104:9795-9810 (2000); and O. Siiman et al, *Cytometry*, 41:298-307 (2000). An alternative to this coated substrate employs carboxyfuictionalized polystyrene particles as the core substrate, coated with aminodextran by EDAC coupling as described in U.S. Pat. No. 5,639,620. These and other solid supports are known to those of skill in the art and are available from a variety of commercial sources, including, without limitation, Amersham Pharmacia (Uppsula, Sweden); Pierce; Bio-rad (Richmond, Va.), and Beckman Coulter, among others.

In one embodiment, the solid support is composed of activated sepharose. CnBr-activated sepharose may be purchased from Amersham Pharmacia. However, other sources of sepharose and activated sepharose are known, as are methods of activation and activation compounds. Examples of suitable activated sepharose include CnBr-, carbonyldiimidazole-, glutaraldehyde-, hydroxysuccinimide-, and tosyl chloride-activated sepharose.

Methods for binding the sialic acid, or the molecule comprising sialic acid (e.g., mucin), to the solid support may be selected from among known methods. Such methods are also provided by the manufacturers of the solid supports.

In one embodiment, the mucin-linked solid support is loaded in an affinity column for separation, isolation and/or purification of a protein containing sialic acid binding sites. In this embodiment, a sample containing the purification target (e.g., lysate from an AAV4 cell culture) is allowed to flow through the column so that the purification target specifically binds to the mucin-linked solid support. Thereafter, the column is washed to remove non-specifically bound material, while retaining the specifically bound purification target. Desirably, the wash reagent is saline, or another suitable reagent, which is buffered to physiologic pH (e.g., phosphate buffered saline). The column is then subjected to a further washing step under conditions which remove the purification target. Suitably, the elution reagent is a solution containing high concentrations of salt. One suitable example, is a phosphate buffered saline solution containing NaCl at concentrations of at least about 0.1M. Another suitable solution contains phosphate buffered saline and at least about 0.4 M NaCl. Given this information, one of skill in the art can readily select an alternative salt solution which will achieve similar effect. Alternatively, the elution reagent may be any suitable acidic reagent, or salt thereof, (e.g., a reagent having a low pH in the range of about 1 to about 5. Examples of such reagents include acetic acid (e.g., 1 mM) and salts thereof such as sodium acetate, and 0.1 M glycine (pH 3), among others which will be readily apparent to those of skill in the art. Following elution of the purification target (e.g., AAV5), the AAV5 may be subject to concentration by conventional techniques.

In another embodiment, the mucin-linked solid support (or the solid support linked to another desired sialic-acid containing molecule) may be incubated with a sample containing the purification target. In such an embodiment, the sample may be a solution containing the lysate from a cellular culture in which the protein to be isolated was produced. Alternatively, the sample may be a biological sample from a subject, or a biological sample from a subject in admixture with a suitable diluent.

The "biological samples from a subject" of the invention can include any sample includes, among other fluids, whole blood, plasma or serum, where the formed bodies are cells, particularly blood cells. Such samples may be purified by conventional methods, such as separation by centrifugation, etc., for the handling of other samples of that type. These "biological samples from a subject" may be mixed with labeling compounds and/or mixed with optionally buffers or diluents in order to adjust the concentration of the sample, or otherwise prepare the sample for analysis. In yet another alternatively, the biological sample may be a tissue sample, and the mucin-linked solid support may be admixed with a suitable buffer or other diluent for incubation with the tissue sample.

Purification and Diagnostic Kits

In another embodiment, the invention provides a kit useful for separating the purification target. This kit is particularly well adapted for use in production of viral vectors (e.g., AAV4 or AAV5).

Typically, such a kit contains a solid support having sialic acid or a sialic-acid containing molecule linked thereto. Such solid supports may be selected from among these described above. In one desirable embodiment, the solid support is a bead or gel for incubation with the sample. In another desirable embodiment, the solid support is loaded in an affinity column (e.g., a liquid chromatography column), and the sample is passed through the column.

In addition, a kit of the invention may also contain the desired reagents, including wash reagents, elution reagents, and concentration reagents. Such reagents may be readily selected from among the reagents described herein, and from among conventional concentration reagents. In one desirable embodiment, the wash reagent is an isotonic saline solution which has been buffered to physiologic pH, such as phosphate buffered saline (PBS); the elution reagent is PBS containing 0.4 M NaCl, and the concentration reagents and devices. For example, one of skill in the art will recognize that reagents such as polyethylene glycol (PEG), or $NH_4SO_4$ may be useful, or that devices such as filter devices. For example, a filter device with a 100 K membrane would concentrate rAAV.

These kits may additionally contain reagents necessary to maintain or preserve the samples. More importantly, the kit contains instructions for performing the competitive assay and preparing the controls. Also provided in a kit may be suitable diluents and buffers for the samples, indicator charts for signal comparisons, disposable gloves, decontamination instructions, applicator sticks or containers, and sample preparator cups. The kits preferably also contain necessary buffer substances or media, as required. One of skill in the art could assemble any number of kits with the information and components necessary to perform the method on a patient for any specific receptor and target cell, and compare the results to norms for that binding site.

In still another embodiment, the invention provides a kit useful for detecting the presence of the purification target (e.g., AAV2/5) in a sample. In addition to containing the components described above, such a kit may also contain a marker reagent which permits visual detection of binding of the purification target to the molecule. This kit is particularly well adapted for detection of purification target in a biological sample from a subject, e.g., the blood. This type of kit, in addition to containing the sialic acid-linked support and reagents described above, may further include markers which are visually detectable.

The term "markers" generally refers to molecules, preferably proteinaceous molecules, but also small chemical molecules, preferably those which are visually detectable. In one example, these markers enable detection by emitting a detectable signal of a particular wavelength upon excitation by a laser. Phycobiliproteins, tandem dyes, certain fluorescent proteins, small chemical molecules, and certain molecules detectable by other means can all be considered markers for these analyses. See, e.g., the markers listed in

*Handbook of Fluorescent Probes and Research Chemicals*, 6th Ed., R. P. Haugland, Molecular Probes, Inc., Eugene, Oreg. (1996).

Examples of phycobiliproteins useful in the present invention are phycocyanin, allophycocyanin (APC), allophycocyanin B, phycoerythrin (PE) and preferably R-phycoerythrin. PE is among the brightest fluorescent dyes currently available. Conjugated to an antibody, PE has been used to detect interleukin-4 in a fluorescent plate assay and in M. C. Custer and M. T. Lotze, *J. Immunol. Meth.*, 128, 109-117 (1990), and found to be the only tested fluorophore that produced adequate signal. The tandem dyes are non-naturally occurring molecules that may be formed of a phycobiliprotein and another dye. See, for example, U.S. Pat. No. 4,542,104 and U.S. Pat. No. 5,272,257. Examples of tandem dyes useful in the present invention are phycoerythrocyanin or PC5 (PE-Cy5, phycoerythrin-cyanin 5.1; excitation, 486-580 nm, emission, 660-680 nm) [A. S. Waggoner et al, *Ann. N.Y. Acad. Sci.*, 677:185-193 (1993) and U.S. Pat. No. 5,171,846] and ECD (phycoerythrin-texas red; excitation, 486-575 nm, emission, 610-635 nm) [U.S. Pat. No. 4,542,104 and U.S. Pat. No. 5,272,257]. Other known tandem dyes are PE-Cy7, APC-Cy5, and APC-Cy7 [M. Roederer et al, *Cytometry*, 24:191-197 (1996)]. Tandem dyes, PC5 and ECD, have been successfully directly conjugated to monoclonal antibodies by several methods that involve iminothiolane activation of the dye. Still other markers which may be directly conjugated to a ligand and used with the phycobiliproteins or tandem dyes in this invention to add additional numbers of markers (labeled ligands) to the method include small molecules which upon excitation emit wavelengths of less than 550 nm. Such molecules do not overlap with the emissions of the phycobiliproteins. One example of such a marker is fluorescein isothiocyanate (FITC). Others are listed in the Handbook cited above. Still other markers which may be employed in this method to provide additional colors are the proteins known as the green fluorescent proteins and blue fluorescent proteins; also useful may be markers which emit upon excitation by ultraviolet light. The biliproteins and tandem dyes are commercially available from various sources including Coulter International Corporation, Miami, Fla., Molecular Probes, Inc., Eugene, Oreg. and Prozyme, Inc., San Leandro, Calif. The other markers or labels discussed above may be obtained commercially from known sources.

The methods for utilizing these markers will be readily apparent to those of skill in the art, and may involve incubating the sample in the presence of a marker prior to contacting the sialic acid-linked solid support. Alternatively, the marker may be bound to the solid support. In yet another alternative, the marker may be incubated in the eluate containing the purification target following the wash step which removes the specifically bound purification target from the solid support. The selection of the marker and the detection system are not a limitation of the present invention.

The kits provided by the present invention are useful for performing the methods described herein.

The following examples are provided to illustrate the invention and do not limit the scope thereof.

EXAMPLE 1

Production of Matrix for Vector Purification

To produce a matrix for affinity purification of vectors with an AAV5 capsid, mucin was coupled to CNBr-activated sepharose.

Briefly, 120 mg of mucin type I-S (Sigma, St. Louis, Mich.) was coupled to 3.5 g of CnBr-activated sepharose (Amersham Pharmacia, Uppsala, Sweden) according to manufacturer instructions. The resin (3.5 gm of freeze-dried power+120 mg mucin) was packed in a 2.5 cm diameter liquid chromatography column (Sigma) and washed with 24 mL of PBS, pH 7.4 (Life Technologies, Grand Island, N.Y.).

Recombinant AAV2/5 was produced by transfection in 293 cells of plasmids encoding AAV serotype 2 rep and serotype 5 cap, and Ad helper functions as described (A. Auricchio, et al, *Hum Gene Ther*, 12:71-76 (2001)). Cells from 50×150 mm plates were harvested, resuspended in 2.5 ml of serum-free DMEM/plate and lysed by two rounds of freezing and thawing. The resulting viral vector contains AAV2 inverted terminal repeats flanking the gene indicated in Table 1 (β-galactosidase or enhanced green fluorescent protein (EGFP)) and other vector elements, in a capsid protein of AAV serotype 5. Prior to application onto the affinity column the lysate containing the AAV2/5 vector was treated as described for AAV2 (Auricchio, et al cited above).

The filtered lysate was allowed to flow through the column at a rate of 1 drop/second, followed by 2 washes of PBS (20 ml) and elution with PBS+0.4M NaCl (15 ml). The eluate was concentrated to 2-3 ml through a Millipore filter-device, washed once with 15 ml of PBS and re-concentrated to a final volume of 2-3 ml to exchange buffer.

Characterization of the AAV2/5 vector preps included physical titers (genome copies), transducing titers after limiting dilution infections on 293 cells and infectious center assays (Table I). Genome copies were determined by real time PCR as described (G. Gao, et al, *Hum Gene Ther*, 11:2079-2091 (2000)). Infectious units were measured following limiting dilution infection of rep-cap expressing cell line in the presence of adenovirus as described (G. Gao, et al, cited above).

TABLE I

Comparison of yields and infectivity of AAV2/5 purified by $CsCl_2$ gradients vs affinity column.

| | # | Purif. | GC/ml | Yield | TU/ml | GC/IU |
|---|---|---|---|---|---|---|
| CMV.lacZ | AA116 | $CsCl_2$ | $5.2 \times 10^{12}$ | $1.56 \times 10^{13}$ | $3.8 \times 10^7$ | 288 |
| CMV.lacZ | AA115 | column | $1.8 \times 10^{12}$ | $8.1 \times 10^{12}$ | $2.1 \times 10^7$ | 180 |
| CMV.lacZ | AA109 | column | $6 \times 10^{11}$ | $2.4 \times 10^{13}$ | $1 \times 10^7$ | 300 |
| CMV.EGF | AA72 | $CsCl_2$ | $1.3 \times 10^{12}$ | $1.95 \times 10^{12}$ | $2 \times 10^7$ | 928 |
| CMV.EGF | AA131 | column | $5.6 \times 10^{12}$ | $2.52 \times 10^{13}$ | $2.2 \times 10^7$ | 1600 |

TABLE I-continued

Comparison of yields and infectivity of AAV2/5 purified by
CsCl₂ gradients vs affinity column.

| | # | Purif. | GC/ml | Yield | TU/ml | GC/IU |
|---|---|---|---|---|---|---|
| CMV.EGF | AA139 | column | $3.8 \times 10^{12}$ | $2 \times 10^{13}$ | $4 \times 10^{7}$ | 1055 |
| CMV.EGF | AA144 | column | $3.2 \times 10^{12}$ | $9.6 \times 10^{12}$ | $3.8 \times 10^{7}$ | 547 |

NB. GC, genome copies;
TU, transducing units;
IU, infectious units;
CMV, cytomegalovirus promoter;
EGFP, enhanced green fluorescent protein.

EXAMPLE 2

Ability of Invention to Differentiate Between AAV2/5 and AAV2

To test the hypothesis that mucin could efficiently bind to vectors bearing an AAV5 capsid, AAV2/5 or AAV2 particles were preabsorbed with soluble mucin and then tested for infectivity on target cells as follows.

$1 \times 10^{10}$ genome copies (GC) of either AAV2/5- or AAV2-CMV-EGFP were incubated (or not) for one hour at 37° C. with 20 mg mucin/ml in Dulbecco-modified Eagle's medium prior to infection of 293 cells. Forty-eight hours later, transduced cells were evaluated under a fluorescence microscope using a triple filter (allowing for visualization of DAPI-FITC and rhodamine).

Mucin was observed to inhibit transduction of 293 cells by AAV2/5 but not AAV2, indicating that the sialic acid component of this protein was able to block the AAV5 capsid binding sites. Thus, the invention provides a method for readily separating AAV5 from AAV2 and other cellular, proteinaceous, and viral materials which lack the ability to bind sialic acid.

EXAMPLE 3

In Vitro Comparison of AAV2/5 Vectors Isolated by Mucin Column of Invention Vs. Prior Art Method Yields, transduction efficiency and infectivity characteristics evaluated in vitro are comparable between AAV2/5 vectors purified using CsCl₂ sedimentation and the mucin column of the invention.

Preps AA115 and 116 were produced from a common vector-containing cell lysate and divided in two equal fractions. AAV2/5-CMV-lacZ vectors were either purified by CsCl₂ (AA116) or mucin column (AA115) purification of AAV2/5 to evaluate their ability to infect differentiated human airway epithelia from the apical side. One week after transduction, the vectors were purified by physical gradients or the mucin column of the invention, and X-gal staining was performed.

The purity of the AAV2/5 purified by the mucin column according to the invention was compared to those obtained by CsCl₂ using SDS-polyacrylamide gel (4-12% SDS PAGE) followed by Comassie-blue staining to visualize proteins. The only bands detected in the column purified preparations represent the capsid proteins VP1, 2 and 3 as opposed to what was observed in the CsCl₂-purified preparations which contained a number of contaminating proteins. The number of blue-forming units (i.e., X-gal expressing cells, bfu) was similar between CsCl₂-(54.6 bfu/$1 \times 10^{10}$ GC) and column-purified vector (58 bfu/$1 \times 10^{10}$ GC).

EXAMPLE 4

In Vivo Comparison of Vectors Isolated by Mucin Column of Invention Vs. Prior Art Method The infectivity of AAV2/5 vectors purified by CsCl₂ (prep AA116) and mucin (AA115) were evaluated in vivo following injection into skeletal muscles as follows and lacZ expression was quantified by ELISA of homogenates or X-gal staining of histological sections.

Six-week-old male C57B1/6 mice were injected in the tibialis anterioris of both legs with $1 \times 10^{11}$ GC of AAV2-CMV-lacZ either purified by mucin column or CsCl₂ gradients. Twenty-one days after vector administration, the right muscles were harvested, sectioned and X-gal stained.

The similarity in intensity and number of β-gal positive muscle cells administered CsCl₂- and the vectors purified by mucin column according to the invention was confirmed by the ELISA quantification of β-galactosidase (CsCl₂: N=5, 113±13 ng/ml; mucin column: N=5, 183±123 ng/ml).

This indicates that the purification method of the invention has no detrimental impact on the infectivity of the viral constructs purified thereby.

All publications cited in this specification are incorporated by reference herein. While the invention has been described with reference to a particularly preferred embodiment, it will be appreciated that modifications can be made without departing from the spirit of the invention. Such modifications are intended to fall within the scope of the appended claims.

What is claimed is:

1. A method for isolating a purification target comprising a protein which specifically binds sialic acid, said method comprising the step of:

allowing the purification target to contact a molecule comprising sialic acid which has been linked to a solid support, whereby the purification target having a binding site for sialic acid is selectively bound by the molecule, wherein the purification target comprises a capsid protein selected from the group consisting of an AAV serotype 4 capsid protein, an AAV serotype 5 capsid protein, and a capsid comprising a fragment of an AAV4 or AAV5 capsid which contains the binding site for sialic acid.

2. The method according to claim 1, wherein the molecule comprising sialic acid is mucin.

3. The method according to claim 1, wherein the solid support is selected from the group consisting of sepharose, agarose, and a polyacrylamide resin.

4. The method according to claim 1, wherein the purification target and the solid support are contacted by incubating a solution comprising the AAV and cellular materials and the support.

5. The method according to claim 1, wherein the solid support is packed in a liquid chromatography column.

6. The method according to claim 1, further comprising the step of washing the solid support to remove material from the mixture which is non-specifically bound to the molecule-linked support.

7. The method according to claim 1, further comprising the step of separating the purification target from the solid support.

8. A method for isolating a viral vector having a protein with a binding site for sialic acid from a mixture, said method comprising the steps of:
  (a) allowing a mixture which contains the viral vector to contact mucin which has been linked to a solid support, whereby the virus is selectively bound by the mucin-linked support, and
  (b) washing the solid support to remove material from the mixture which is non-specifically bound to the mucin-linked support;
  (c) washing the solid support to separate the viral vector from the solid support using a concentrated salt solution of phosphate buffered saline and 0.4 M sodium chloride.

9. The method according to claim 8, further comprising the step of concentrating the viral vector following separating.

10. The method according to claim 8, wherein the protein is selected from the group consisting of an AAV serotype 4 capsid protein, an AAV serotype 5 capsid protein, and a capsid comprising a fragment of an AAV4 or AAV5 capsid which contains the binding site for sialic acid.

11. A kit useful for detecting a purification target in a mixture, said kit comprising a sialic acid linked to a solid support comprising activated agarose with mucin linked thereto and a reagent which permits visual detection of binding of the purification target to a molecule comprising sialic acid, wherein the purification target comprises a protein selected from the group consisting of an AAV serotype 4 capsid protein, an AAV serotype 5 capsid protein, or a fragment of an AAV4 or AAV5 capsid protein having a binding site for sialic acid.

12. The kit according to claim 11, wherein the solid support is loaded in an affinity column.

13. The kit according to claim 12, wherein the affinity column is a liquid chromatography column.

14. The kit according to claim 11, wherein the kit further comprises wash, elution, and concentration reagents.

15. A method of detecting in a sample the presence of a virus with a surface protein selected from an adeno-associated virus (AAV) serotype 4 capsid protein or AAV serotype 5 capsid protein, or fragment thereof, said method comprising the step of utilizing the kit of claim 11 on a sample to visually detect binding of the virus.

16. A composition useful in binding a purification target from a mixture comprising at least one 2-3,O-sialic acid moiety and at least one 2,3-N-sialic acid moiety linked to a solid support.

17. A method of binding an adeno-associated viral (AAV) vector having an AAV serotype 4 protein or an AAV serotype 5 capsid protein from a culture, said method comprising the step of incubating the composition of claim 16 on lysate or media from the culture.

18. The method according to claim 3, wherein the solid support is sepharose activated with a compound selected from the group consisting of CnBr, carbonyldiimidazole, glutaraldehyde, hydroxysuccinimide, and tosyl chloride.

19. The method according to claim 7, further comprising the step of concentrating the separated purification target.

* * * * *

UNITED STATES PATENT AND TRADEMARK OFFICE
CERTIFICATE OF CORRECTION

| | |
|---|---|
| PATENT NO. | : 7,319,002 B2 |
| APPLICATION NO. | : 10/485893 |
| DATED | : January 15, 2008 |
| INVENTOR(S) | : James M. Wilson et al. |

Page 1 of 1

It is certified that error appears in the above-identified patent and that said Letters Patent is hereby corrected as shown below:

On the Title Page Item - 86 - § 371 (c)(1), (2), (4) date: "Feb. 4, 2004" replace with -- Feb. 5, 2004 --;

Signed and Sealed this

Twentieth Day of May, 2008

JON W. DUDAS
*Director of the United States Patent and Trademark Office*